United States Patent [19]

Brooks

[11] 4,340,602
[45] Jul. 20, 1982

[54] COMPOSITIONS INHIBITING ESTROGEN SULFOTRANSFERASE ACTIVITY

[75] Inventor: Samuel C. Brooks, Detroit, Mich.

[73] Assignee: Wayne State University, Detroit, Mich.

[21] Appl. No.: 952,592

[22] Filed: Oct. 18, 1978

[51] Int. Cl.³ ..................... A01N 45/00; A61K 31/56
[52] U.S. Cl. ..................................... 424/238; 424/243
[58] Field of Search ..................... /Steroids MS File; 424/238, 239, 243

[56] References Cited

U.S. PATENT DOCUMENTS 3,251,833  5/1966  Cantrall et al. ................... 260/239.5
3,813,418  5/1974  Hofmeister et al. ............. 260/397.4
3,939,186  2/1976  Wakabayashi et al. .......... 260/397.4

OTHER PUBLICATIONS

Rozkin et al., "Jour. Biol. Chemistry", vol. 252, No. 20 (1977), pp. 7214–7220.
Tomson et al., "Journal of Org. Chem." (1959), No. 24, pp. 2056–2058.

Primary Examiner—Elbert L. Roberts
Attorney, Agent, or Firm—Joan Thierstein; Sidney B. Williams, Jr.

[57] ABSTRACT

An estrogen sulfotransferase inhibitor composition comprises a compound of the formula

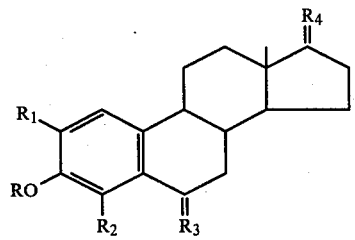

wherein $R_1$ is Br, $NO_2$, or H; $R_2$ is Br, $NO_2$, $NH_2$, or H; R is H or alkyl of 1-4 carbon atoms; $R_3$ is O or $H_2$; and $R_4$ is $H_2$, O, or α-H, β-OH, in admixture with a pharmaceutically acceptable carrier. The specificity of the invention is believed targeted to the substituent at $R_2$ or $C_4$ and secondarily the OR group at $C_3$.

24 Claims, 2 Drawing Figures

COMPOSITIONS INHIBITING ESTROGEN SULFOTRANSFERASE ACTIVITY

The invention described herein was made in the course of work under a Public Health Service Grant CA-13645 and HD-8735 from the Department of Health, Education and Welfare.

BACKGROUND OF THE INVENTION

This invention relates to compositions adaptable to terminating a pregnancy of a higher female primate having a defined menstrual or estrous cycle by administration to the pregnant female of a contragestative agent, which has estrogen sulfotransferase inhibitory activity and which prevents implantation.

The use of chemical agents to prevent or suppress fertility in warm-blooded female mammals is widely practiced in the medical art. The most widely used of these chemical agents comprise mixtures of steroidal estrogens and progestins. These agents produce a type of pseudopregnancy which prevents normal ovulation from occurring in the female taking the medication. Although these agents are very effective, noticeable and irritating side effects, including nausea, gastric disturbances, headache, dizziness, breast discomfort, fluid retention, and vascular disorders, are often produced.

Contraception has also been brought about by impairing the luteal phase of the endometrium. A properly prepared endometrium or uterine lining is required for the blastocysts to become successfully implanted. Agents can act either to interfere with the formation of the luteal or secretory phase of the endometrium. In an alternate mode of action agents delay or decrease formation of the luteal phase of the uterine lining. The result is desynchronization of uterine development with respect to blastocyst implantation or nidation.

Intrauterine devices of various kinds have also been used to prevent pregnancy. These devices must be inserted by qualified medical practitioners. Moreover, they are not totally reliable as a means of preventing pregnancy because intrauterine devices can be involuntarily expelled without knowledge of the patient. In other cases the devices may cause intrauterine irritation or bleeding.

Another type of contraceptive practice known to the medical profession is administration of an estrogen, e.g., diethylstilbesterol or ethinyl estradiol. These are the so-called "morning-after pill," because they are used as post-coital contraceptive agents. These agents are thought to be effective because they interfere with the transport mechanism of the fertilized ovum through the Fallopian tubes and result in premature expulsion of the fertilized ovum (blastocyst) from the Fallopian tubes or because they reverse the differentiation of the endometrium from secretory back to proliferative.

Because of the annoying and sometimes serious side effects of currently used anti-fertility agents, there is a need for chemical agents which will prevent pregnancy and for new and better methods of administering existing anti-fertility agents. Particularly, there is a need for highly effective compounds which can be administered to a female patient who suspects that she is in the early stages of pregnancy, but which otherwise requires minimal exposure of the patient to powerful steroidal medication.

It is an object of this invention to provide highly effective contragestative agents for higher primates having a well-defined menstrual or estrous cycle. These compounds are therefore effective for terminating pregnancies at a very early stage. Unlike widely used "pill" formulations, which must be administered in anticipation of coitus, the compounds used in the method of the present invention are administered only when needed and then only for a relatively short time before or at the expected time of implantation.

PRIOR ART STATEMENT

Typical regimens for preventing pregnancy include those disclosed by Applezweig (U.S. Pat. No. 3,409,721), Ijzerman (U.S. Pat. No. 3,502,772) and Rochefort (U.S. Pat. No. 3,795,734).

The use of 7α-methyl-estr-5-ene-3β,17-diol as a contragestative agent is disclosed in U.S. Pat. No. 4,073,899 (Grunwell et al).

Lange-Sundermann (U.S. Pat. No. 3,236,731) indicates that $\Delta^4$-pregnene-6β,20β-diol-3-one and allopregnane-20β-ol-3,6-dione are rapidly acting agents against amenorrhea.

Mehrhof et al (U.S. Pat. No. 3,639,599) employ a combination of estrone sulfate and estradiol-3-sulfate as a uterotropic composition.

Cantrall et al (U.S. Pat. No. 3,377,362) indicate that 1-bromo-3-methoxy-estra-1,3,5(10)-triene-17-one and related compounds have estrogenic activity.

Hofmeister et al (U.S. Pat. No. 3,813,418) disclose a synthetic route to estrogenic 6-keto-$\Delta^{1,3,5(10)}$ steroids.

Deason (U.S. Pat. No. 3,501,506) is cited for a disclosure of 2-mercapto 17-oxygenated-estra-1,3,5(10)-trienes having estrogenic activity.

Weichert et al (U.S. Pat. No. 3,789,087) is of interest with respect to 4,6-dichloro-$\Delta^{4,6}$-steroids of the pregnane and androstane series.

Pertinent literature references include:

Brooks et al, "Role of Sulfate Conjugation in Estrogen Metabolism and Activity," *J. Toxic. and Environ. Health*, 4:283-300 (1978).

Rozhin et al "Studies on Bovine Adrenal Estrogen Sulfotransferase: II. Inhibition and Possible Involvement of Adenine-estrogen Stacking," *J. Biol. Chem.*, 252:7214-7220 (1977).

Pack et al, "Cyclic Activity of Estrogen Sulfotransferase in the Gilt Uterus," *Endocrinology*, 95:1680-1690 (1974).

Pack et al, "Nuclear and Cytoplasmic Estrogen Receptor in Gilt Endometrium Throughout the Estrous Cycle," *Endocrinology*, in press (1978).

Pack et al, "The Metabolism and Nuclear Migration of Estrogen in Porcine Uterus Throughout the Implantation Process," *Biol. of Reprod.*, in press (1979)

Pack et al, "The Cyclic Relationship of Estrogen Sulfurylation to the Nuclear Receptor Level in Human Endometrial Curettings," *J. Clin. Endocrin. and Metab.*, submitted 1978.

SUMMARY OF THE INVENTION

This invention relates to an estrogen sulfotransferase inhibitor composition, comprising a compound of the formula wherein $R_1$ is Br, $NO_2$, or H; $R_2$ is Br, $NO_2$, $NH_2$, or H; R is H or alkyl of 1–4 carbon atoms; $R_3$ is O or $H_2$; and $R_4$ is $H_2$, O, or $\alpha$-H,$\beta$-OH, in admixture with a pharmaceutically acceptable carrier.

This invention further relates to a method of terminating a pregnancy comprising preventing implantation of a blastocyst in the epithelial uterine lining of a pregnant female by administering to the pregnant female during the period of implantation an amount of an estrogen sulfotransferase inhibitor, as above, effective to prevent implantation.

DETAILED DESCRIPTION

As used in the specification and claims, "higher primate" includes those primate species in which the female generally has a predictable menstrual or estrous cycle. These species include the human, Rhesus monkey, orangutan, chimpanzee, etc.

The method of the present invention may be used for other mammlian species, including bovine and porcine animals.

Pregnancy is a condition of the female mammal in which a fertilized ovum is contained in her reproductive tract. For the purposes of this invention, the period of gestation or pregnancy is defined as beginning at the point of fertilization.

Nidation, as used in the specification and claims, means the period of time in which the fertilized ovum (blastocyst) attaches itself to and penetrates within the epithelial lining of the uterus.

Implantation, as used in the specification and claims, means the period of time in which the blastocyst begins to form a placental membrane and to establish a direct connection with the blood supply of the mother. Although the exact process by which the active material is employed in the practice of this invention in terminating a pregnancy is unclear, it appears that the method of this invention interferes with the implantation process by decreasing the ability of the mother or support the life of the blastocyst. Thus, the gestation period is interrupted at a very early stage. Therefore, the method of this invention is to be considered as a method of preventing implantation or of contragestation, rather than as a method of abortion.

Materials usable for the practice of this invention are those which inhibit estrogen sulfotransferase, particularly uterine estrogen sulfotransferase. Inhibitors include, but are not limited to, compounds of the formula wherein $R_1$ is Br, $NO_2$, or H; $R_2$ is Br, $NO_2$, $NH_2$, or H; R is H or alkyl of 1–4 carbon atoms; $R_3$ is O or $H_2$; and $R_4$ is $H_2$, O, or $\alpha$-H,$\beta$-OH, in admixture with a pharmaceutically acceptable carrier. The substituent at $R_2$ is deemed critical.

Preferred compounds for the practice of the invention are those wherein:
(a) R is methyl;
(b) $R_1$ is H, including (a);
(c) $R_1$ is Br, $NO_2$ or $NH_2$, including (a);
(d) $R_2$ is Br, including each of (a)–(c);
(e) $R_2$ is $NO_2$, including each of (a)–(c);
(f) $R_2$ is $NH_2$, including each of (a)–(c);
(g) $R_3$ is O, including each of (a)–(f);
(h) $R_3$ is $H_2$, including each of (a)–(f);
(i) $R_4$ is O, including each of (a)–(h); and
(j) $R_4$ is $\alpha$-H,$\beta$-OH, including each of (a)–(h).

Particularly preferred compounds are those wherein:
(a) R is methyl, $R_2$ is $NO_2$ and $R_3$ is O;
(b) R is methyl, $R_1$ and $R_2$ both are Br or $NO_2$ and $R_4$ is O or $\alpha$-H,$\beta$-OH;
(c) R is methyl, $R_1$ is H and $R_2$ is $NH_2$;
(d) R is methyl and $R_4$ is $\alpha$-H,$\beta$-OH;
(e) $R_1$ and $R_2$ are $NO_2$;
(f) $R_1$ and $R_2$ are Br;
(g) R is methyl, $R_1$ is H and $R_4$ is $\alpha$-H,$\beta$-OH.

Most preferred are 2,4-dibromo-1,3,5(10)-estratriene-3,17$\beta$-diol, 4-nitro-1,3,5(10)-estratriene-3,17$\beta$-diol, and 3-methoxy-4nitroestrone.

SYNTHESIS AND EVALUATION SECTION

Compounds which can be used in the practice of the invention are described by Tomson et al, Journal of Organic Chemistry, 24:2056 (1959). These compounds are of the estrone series, but the corresponding 17-alcohols can be obtained by reduction.

Materials are evaluated for activity as estrogen sulfotransferase inhibitors by the method of Rozhin et al, Journal of Biological Chemistry, 252:7214–7220 (October 25, 1977), herein incorporated by reference.

As will be apparent from the examples below, 1,3,5(10)-estratriene compounds having a 3-hydroxyl are the most effective inhibitors. The corresponding compounds having a saturated A ring, e.g., 5-androstene, are inactive as inhibitors. Estrogens having a second hydroxyl group, particularly a 17$\beta$-hydroxyl or a hydroxyl at the 16$\alpha$-or 16$\beta$-position are also good inhibitors. A mechanism by which estrogen sulfotransferase inhibition is achieved is proposed by Brooks et al, Journal of Toxicology and Environmental Health, 4:283–300 (1978), herein incorporated by reference.

Pregnancy in many higher animals, including the human, bovine animals and porcine animals, is characterized by prolongation of the life of the corpus luteum, which continues to secrete progesterone. Owing to a correlation between plasma progesterone level and uterine estrogen sulfotransferase activity in porcine uteri [Pack et al, Endocrinology, 95:1680–1690 (1974)], herein incorporated by reference, studies on enzymatic activity of estrogen sulfotransferase during pregnancy in porcine animals and humans were undertaken. The porcine studies (Pack et al, "The Metabolism and Nuclear Migration of Estrogen in Porcine Uterus Throughout the Implantation Process," in press, Biology of Reproduction, 1979), herein incorporated by reference, indicate that uterine estrogen sulfurylation requires the presence of progesterone. It is proposed that sulfurylation is one of the mechanisms by which estrogen is metabolized and removed from cells so as to prevent continuation of the proliferative process. The resulting secretory endometrium is thought to be a condition related to implantation.

Related experiments with human endometrial curettings (Pack et al, "The Cyclic Relationship of Estrogen Sulfurylation to the Nuclear Receptor Level in Human Endometrial Curettings," submitted to Journal of Clinical Endocrinology and Metabolism) indicate that estrogen sulfotransferase activity is greatly enhanced during the secretory phase. This is thought to be consistent with the fact that uterine estrogen metabolizing enzymes are induced by progesterone and that their activity is maintained throughout the implantation process [Pack et al (1974)].

The active compound or estrogen sulfotransferase inhibitor of this invention may be administered orally, intrauterinally, intravaginally, or parentally. The dosage depends upon factors such as the method of administration, the scheduling of dosages, and the weight and age of the particular primate being treated. Generally, the amount of a single daily dose required to produce an anti-implantation effect is a dosage of from 0.1–500 mg of active ingredient. Dosage forms may be administered one or more times per day for one day or, preferably, for several days during the period of administration.

In the practice of this invention, the active compounds are administered during the period of implantation immediately prior to the period of nidation. In higher female primates, which have a 26–32 day menstrual cycle, the nidation period is about days 18–23 of the menstrual cycle, counting the onset of the previous menstruation as the first day of the menstrual cycle. The period of implantation is considered as beginning near the 21st day of the same cycle. Within 14 days, placental circulation is usually considered to be complete.

In the human female, nidation commonly occurs on or about the 20th day of the cycle. Implantation generally occurs a day later, about the 21st day, of the same cycle. By about the 35th day, placental circulation is considered to be completed. Accordingly, the compounds of the present invention are administered on or about 21 days after the onset of menstrual bleeding. Administration can be continued daily for 3–9 days during the days 21–35 of the particular menstrual cycle. Preferably, the active compounds are administered for 6–8 days.

Compounds used in the practice of the invention can be administered in various unit dosage forms. They may be taken orally in the form of lozenges or troches containing an inert diluent or other physiologically acceptable edible carrier. If intravaginal administration is selected, local absorption by the vaginal and cervical mucosa will take place. Preparations for this purpose include vaginal creams, jellies and ointments. Topical ointments containing the active ingredient in an ointment base such as petrolatum, lanolin, polyethylene glycol or mixtures thereof are typical of those used for this mode of administration. Generally, the active steroidal sulfotransferase inhibitor is finely divided by milling or grinding and then admixed with the carrier.

Creams and lotions are also acceptable for intravaginal administration. These are prepared by dispensing the active ingredient in an oily phase and forming an emulsion therefrom. A formulation which is preferred for vaginal administration is a stable, non-aqueous, aerosol foam which readily collapses at body temperatures and spreads as a uniform film along the vaginal walls. These compositions are considered to be cosmetically superior to other formulations because they do not produce a sensation of warmth or dehydration when applied. Also, they are neither greasy nor tacky and will not stain clothing. Soft cushiony foams can be prepared and administered intravaginally.

The medicaments used in the practice of this invention can also be administered in a medicated tampon containing the active ingredient. The tampon is applied on or about the expected date of the menstrual period. The active ingredient is released at an acceptable predetermined rate.

If a pregnancy had occurred, release of the active ingredient and its subsequent absorption serves to prevent implantation of the blastocyst and terminate the pregnancy and produce a normal menstrual period.

Without further elaboration, it is believed that one skilled in the art can, using the preceding description, utilizes the present invention to its fullest extent. The following preferred specific embodiments are therefore to be construed as merely illustrative and not limitative of the remainder of the specification and claims in any way whatsoever.

EXAMPLE 1

Determination of Inhibition of Bovine Adrenal Estrogen Sulfotransferase

A. Materials and Methods

Steroids. Commercially available steroids of the highest purity were used. The purity was checked by thin layer chromatography. Estrone sulfate (Sigma Chemical Co.) was recrystallized from a hot methanol solution by the addition of anhydrous ether [Joseph et al, Steroids, Vol. 7, 577–587 (1966)].

Solvents. All solvents used for extractions before chromatography were distilled.

Labeled Compounds. [6,7-$^3$H]Estrone (2.78 Ci/mmol), [6,7-$^3$H]estrone sulfate (2.5 Ci/mmol), and adenosine 3'-phosphate-5'-phospho[$^{35}$S]sulfate (0.4 Ci/mmol) were purchased from New England Nuclear Corp.

Adenosine 3'-phosphate-5'-phosphosulfate. P-Ado-PS was synthesized enzymatically using rat liver 100,000×g supernatant [Rozhin et al, J. Biol. Chem., 249:2079–2087 (1974)] or utilizing a modified procedure of Cherniak et al, J. Biol. Chem., 239:2986–2990 (1964) or Horwitz et al, Biochim. Biophys. Acta, 480:376–381 (1977).

Isolation of Estrogen Sulfotransferase (EC 2.8.2.4). The enzyme was isolated from the bovine adrenals and purified by ammonium sulfate fractionation and column chromatography on DEAE-cellulose or DEAE-Sephadex A-50 [Rozhin et al (1974)].

Standard Enzyme Assay. The incubation mixtures contained the following in a total volume of 0.2 ml: 0.4 mM P-Ado-PS; 2 to 23 µM estrone (3-hydroxy-1,3,5(10)-estratriene-17-one), $5\times10^5$ dpm of [6,7-$^3$H]estrone; 5 mM magnesium acetate; 0.19 M Tris/HCl buffer (pH 8.1 at 37°); 5 ug of the enzyme; and 25 µM dithiothreitol. After a 10-min incubation (in the presence of a constant amount of inhibitor and a variable amount of estrone), the boiled mixtures were supplemented with 5 µg of aqueous estrone sulfate. The remaining [$^3$H]estrone was extracted three times with 0.3 ml of ethyl ether. The residual ether was removed and the volume adjusted to 0.5 ml with methanol. A sample (25 µl) was applied, together with 10 µg of methanolic estrone sulfate marker, to type SG chromatography media (Gelman Instrument Co., Ann Arbor, Mich.), and developed with chloroform/acetone/acetic acid (110:35:6). After drying the sheet, samples were visualized by spraying with methylene blue (25 mg in 100 ml of 0.05 N H$_2$SO$_4$), punched out with a cork borer, and counted in 10 ml of dioxane counting liquid. A blank employing a boiled enzyme sample was incubated and the recorded counts were substracted from each determination. The total corrected counts, representing steroid sulfate ester, were converted to nanomoles utilizing the specific activity of [$^3$H]estrone. An enzyme unit was defined as that quantity of enzyme which synthesized 1 nmol of estrone sulfate in 1 min under chosen conditions. The recovery of [$^3$H]estrone sulfate added to the incubation mixture was 95%. When nonsubstrate steroids were used as the inhibitors, the procedure for the enzyme assay was as described earlier [Rozhin et al (1974)], utilizing 5 µg of enzyme, P-Ado-[$^{35}$S]PS, and unlabeled estrone.

Data Processing. The initial velocity analysis was carried out keeping the concentration of P-Ado-PS at saturation level, varying the estrone concentration and keeping the concentration of the inhibitor at a fixed level. Preliminary plots of the data were made in the double reciprocal form (1/v versus 1/[S]), and in the form of replots of slopes (and intercepts) versus inhibitor concentration. On the basis of these plots, the proper inhibition pattern was chosen for each experiment and the data points were fitted to the appropriate equation.

Linear competitive inhibition:

$$v_i = \frac{V_{max}[S]}{K_m(1 + [I]/K_i) + [S]} \quad (1)$$

Hyperbolic competitive inhibition:

$$v_i = \frac{V_{max}[S]}{K_m\left(\frac{1 + [I]/K_i \text{ num}}{1 + [I]/K_i \text{ den}}\right) + [S]} \quad (2)$$

Slope-parabolic non-competitive inhibition:

$$v_i = \frac{V_{max}[S]}{K_m(1 + [I]/K_{i1} + [I]^2/K_{i2} + [S](1 + [I]/K_i)} \quad (3)$$

All calculations were performed using Cleland's Fortran programs (*Adv. Enzymol.*, 29:1–32). The programs gave the values of $K_m$, $V_{max}$, and inhibition constants.

B. Results and Discussion

Fractional Inhibition. From kinetic experiments, $K_i$ was calculated as described above under "Data Processing" after making replots of slopes (and/or intercepts) versus inhibitor concentration. When these kinetic experiments were not carried out, the inhibition was expressed as the fractional inhibition, FI, which is the fraction of the total control activity that is inhibited under the conditions specified below and may vary from zero (no inhibition) to unity (complete inhibition). FI is defined as: $FI = 1 - v_i/v$, where v equals the initial velocity of sulfurylation at the substrate concentration, $[S] = K_m = 4.5$ µM, $v_i =$ the initial velocity of sulfurylation in the presence of 5-fold excess of the inhibitor ($[I] = 22.2$ µM). Substituting v and $v_i$ from the corresponding rate equations in the absence of ($v = (V_{max}[S])/(K_m + [S])$) and presence of a (competitive) inhibition (Equation 1), the following relationship for FI is obtained:

$$FI_c = \frac{[I]}{K_i\left(1 + \frac{[S]}{K_m}\right) + [I]}$$

Figure 2:
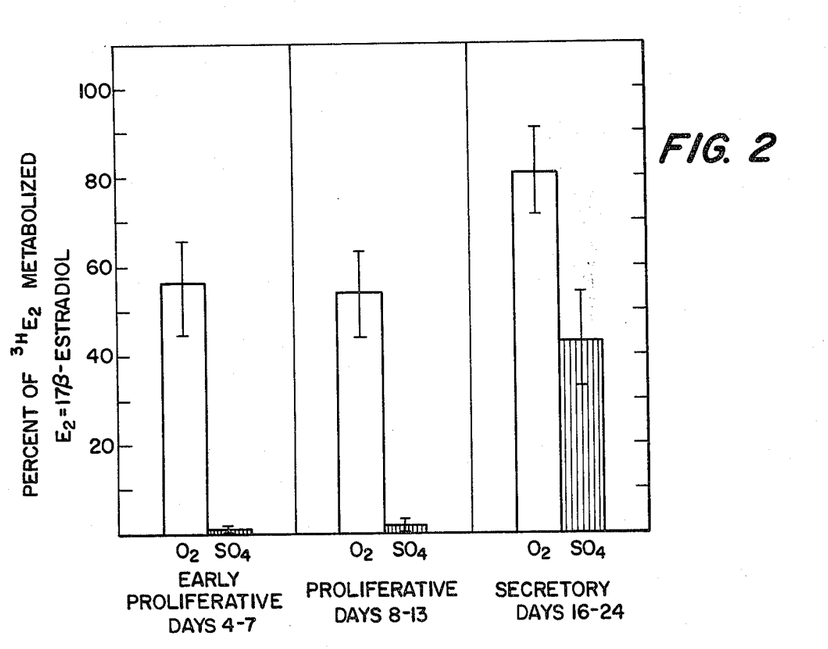
FIG. 2 illustrates the relationship between estradiol metabolism and sulfurylation in human endometrial tissue throughout the menstrual cycle.

After substituting [S], $K_m$, and [I] (see above), the equation for the fractional (competitive) inhibition simplifies to:

$$FI_c = \frac{22.2}{2K_i + 22.2} = \frac{1}{0.09K_i + 1} \quad (4)$$

and the mathematical relationship between FI and $K_i$ of competitive inhibitors is represented by the continuous curve in FIG. 2 in Rozhin et al., J. Biol. Chem., 252, 7214–7220, 1977. The dashed line represents the relationship between FI and the $K_i$ of pure noncompetitive inhibition derived mathematically in an analogous manner and expressed as $$FI_{pnc} = \frac{[I]}{[I] + K_i}$$

Since $[I] = 22.2$ µM, $$FI_{pnc} = \frac{22.2}{222.2 + K_i} = \frac{1}{1 + 0.045 K_i} \quad (5)$$

Within a certain type of inhibition (competitive, non-competitive), the FI is a relative expression of the binding of the compound to the enzyme system.

C. Results

Inhibition constants and fractional inhibition as a function of the oxygenated substituents at the 3- and 17β-positions of estrogens are given in Table I. In Table II are given the same data for substituted estrogen analogs.

TABLE I

Effect of Oxygen Functions in Positions 3 and 17β of Steroids on Inhibition of Estrogen Sulfotransferase

| Steroid | Fractional Inhibition[a] | $K_i$[b] |
|---|---|---|
|  |  | µM |
| 1,3,5(10)Estratriene[c] | 0 | — |
| 1,3,5(10)Estratriene-17β-ol[d] | 0.41 | 16 |
| 1,3,5(10)Estratriene-3-ol[e] | 0.67 | 3.5 |
| 1,3,5(10)Estratriene-3,17β-diol[f] | 0.68 | 6.1 |
| 3-Hydroxy-1,3,5(10)estratriene-17-one[f] | 0.65 | 4.9 |
| 3-Methoxy-1,3,5(10)estratriene-17β-ol[g] | 0.61 | 4.8 |
| 1,3,5(10)Estratriene-3,17β-diol-3-acetate[g] | 0.39 | 17 |

TABLE I-continued

Effect of Oxygen Functions in Positions 3 and 17β of Steroids on Inhibition of Estrogen Sulfotransferase

| Steroid | Fractional Inhibition[a] | $K_i$[b] |
|---|---|---|
| 1,3,5(10)Estratriene-3,17β-diol-3-benzoate[g] | 0.11 | 90 |
| 5-Androstene[h] | 0 | |
| 5-Androstene-3β-ol[h] | 0.31 | 50 |
| 5-Androstene-3β,17β-diol[j] | 0.39 | 35 |
| 3β-Hydroxy-5-androstene-17-one[j] | 0.21 | 170 |
| 5α-Androstane-3β,17β-diol[j] | 0.32 | 47 |
| 17β-Hydroxy-5α-androstane-3-one[j] | 0.37 | 38 |
| 17β-Hydroxy-5β-androstane-3-one[g] | 0.23 | 74 |
| 3β-Hydroxy-5β-androstane-17-one[j] | 0.13 | 302 |

Figure 1:
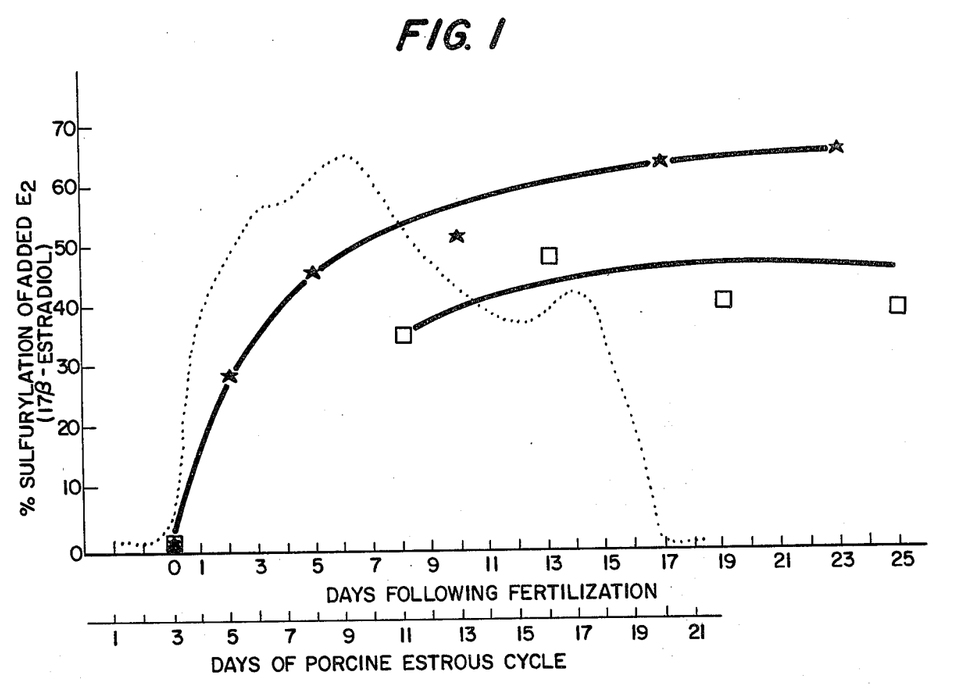
FIG. 1 shows the correlation between estrogen sulfurylation metabolism of gilt and sow whole uterine minces from time of mating through implantation.

[a]The FI is a measure of the inhibition of estrone sulfurylation and may vary from 0 (no inhibition) to 1.0 (complete inhibition).
[b]$K_i$ values for inhibitors 3 to 6, 12, and 16 were determined experimentally (see FIG. 1 and "Materials and Methods" for details of procedure). $K_i$ values for 2, 7, and 8 were calculated from Equation 4 (competitive inhibition); $K_i$ values for 10 and 11 and 13 to 15 were calculated from Equation 5 (noncompetitive-inhibition).
[c]Kenner et al, Journal of the Chemical Society, 522 (1955).
[d]Endocrine Evaluation Branch, Cancer Chemotherapy, National Service Center, Bethesda, MD 20014.
[e]Searle Laboratories, Chicago, Illinois 60680.
[f]Nutritional Biochemicals Corp., Cleveland, Ohio 44128.
[g]Research Plus Steroid Laboratories, Inc., Denville, NJ 07834.
[h]Steroid Reference Collection, c/o Dr. D. F. Johnson, NIH, Bethesda, Maryland 20014.
[i]Schwarz/Mann, Orangeburg, New York 10962.
[j]Sigma Chemical Co., St. Louis, Missouri 63118.

TABLE II

Inhibition of Estrogen Sulfotransferase by Certain Estrogen Analogs

| Steroid | $K_i$[b] (μM) | Fractional Inhibition[c] |
|---|---|---|
| 2,4-Dibromo-1,3,5(10)estratriene-3,17β-diol[d] | 0.11 | 0.99 |
| 4-Nitro-1,3,5(10)estratriene-3,17β-diol[e] | 0.15 | 0.98 |
| 1,3,5(10)Estratriene-3,16α-diol[f] | 1.3 | 0.89 |
| 2-Nitro-1,3,5(10)estratriene-3,17β-diol[e] | 2.4 | 0.80 |
| 2-Amino-1,3,5(10)estratriene-3,17β-diol[e] | 3.5 | 0.76 |
| 4-Amino-1,3,5(10)estratriene-3,17β-diol[e] | 3.5 | 0.76 |
| 2,4-Dinitro-1,3,5(10)estratriene-3,17β-diol[g] | 4.3 | 0.72 |
| 3-Methoxy-4-$NO_2$-1,3,5(10)-estratriene-17-one[g] | 4.3 | 0.72 |
| 3,17β-Dihydroxy-1,3,5(10)-estratriene-6-one[h] | 5.5 | 0.69 |
| 1,3,5(10)Estratriene-3,16β,17β-triol[a] | 5.5 | 0.72 |
| 1,3,5(10)Estratriene-3,16α,17β-triol[h] | 8.2 | 0.66 |
| Diethylstilbestrol[h] | 120 | 0.34 |

[a]Nutritional Biochemicals Corp., Cleveland, Ohio 44128.
[b]$K_i$ values for inhibitors 1 and 5 to 8 were calculated from Equation 4 (competitive inhibition).
[c]The FI is a measure of the inhibition of estrone sulfurylation and may vary from 0 (no inhibition) to 1.0 (complete inhibition).
[d]Research Plus Steroid Laboratories, Inc., Denville, NJ 07834.
[e]Endocrine Evaluation Branch, Cancer Chemotherapy, National Service Center, Bethesda, MD 20014.
[f]Southeastern Biochemicals, Morristown, Tennessee.
[g]Tomson et al, J. Org. Chem., 24:2056 (1959).
[h]Schwarz/Mann, Orangeburg, NY 10962.

EXAMPLE 2

Metabolism of Estrogen in the Porcine Uterus During Implantation

A. Materials and Methods

Animals. Gilts (virgin female pigs) or sows (previously pregnant pigs) in estrus from the pig farm at Michigan State University were mated with boars of established fertility. Following insemination, the females were sacrificed at various times up to 25 days later. Uteri were removed and immediately chilled on ice. Fertilization was confirmed initially by microscopic examination of oviductal washings for fertilized ova (2–5 days following insemination) by histological inspection of the corpus luteum and uterus (8–13 days) and later (17–25 days) by gross inspection of the uterus for the amniotic sac and fetuses.

Radioisotopes. [6,7-$^3$H]$E_2$ (45 Ci/mmol) was obtained from New England Nuclear Corp., Boston, Mass., and purified on ITLC-SA (Gelman Instrument Co.) with $CHCl_3$:$CH_3OH$ (97:3) as the developing solvent. $Na_2^{35}SO_4$ (800–1000 mCi/mmol) was obtained from New England Nuclear Corp. and used directly from the bottle.

Exchange assay for nuclear receptor. The endometrium was scraped from the myometrium by means of a sharp scalpel, placed in ice cold sucrose buffer (0.25 M sucrose, 3 mM $MgCl_2$, 10 mM Tris, pH 7.6), filtered and washed over medium coarse nylon gauze. Four aliquots of tissue (500 mg each) were homogenized in sucrose buffer (3 ml, 0° C.) on a Polytron, two bursts of 15 seconds each at the 4 setting with a one min. interval. The homogenate was filtered through fine nylon gauze, the residue washed with sucrose buffer (2 ml) and the filtrate centrifuged at 800×g for 10 min. at 4° C. After the supernatant was decanted, the pellet was washed with cold sucrose buffer twice (5 ml). The resulting washed nuclei were resuspended in sucrose buffer, from which were taken 1 ml aliquots for receptor studies and DNA analyses by the method of Giles et al, Nature, 206:93 (1965). A small amount was set aside for a nuclei count.

The 1 ml aliquots were centrifuged again at 800×g for 10 min. at 4° C. and the supernatants discarded. Tris-EDTA buffer (10 mM Tris, 1.5 mM EDTA, pH 7.4, 0.7 ml) was added to each chilled tube. A series of standards with final concentrations of [6,7-$^3$H]$E_2$ ranging from 0.25 to 1.5 nM was added in triplicate to half the tubes. To the other half, standards were added containing the same concentrations of [$^3$H]$E_2$ plus 100-fold unlabeled $E_2$. The two series were incubated for 60 min. at 23° C. with shaking. After the incubation, the tubes were placed on ice; 3 ml of Tris-EDTA buffer was added; and they were centrifuged at 100×g for 10 min. The pellet was washed twice with the buffer (3 ml); and the [$^3$H]$E_2$ present was extracted with ethanol (3 ml) overnight at room temperature or for 2 hr at 37° C. After centrifugation, aliquots (2.5 ml) were taken for counting, utilizing a liquid scintillation spectrometer. The data was analyzed by a Lineweaver-Burke plot of 1/nM $E_2$ vs 1/pmoles bound $E_2$, which yielded the binding capacity and dissociation constant ($K_d$).

Incubation and isolation of [$^3$H]$E_2$ and $Na_2^{35}SO_4$ metabolites. Samples of whole uterus (400 mg), minced in 0.9% saline, were filtered over medium coarse nylon gauze and placed in 2.5 ml of a modified Krebs-Ringer bicarbonate buffer ($MgCl_2$ instead of $MgSO_4$) with glucose (1.5 mg/ml). After the [6,7-$^3$H]$E_2$ (3×10$^{-9}$ M) and $Na_2^{35}SO_4$ (1×10$^{-4}$ M) were added, the mixture was incubated for 2 hr at 37° C. under 95% $CO_2$ and 5% $O_2$. The incubate was then boiled for 2 min. to stop the enzymatic reactions. A control was included with each experiment, which contained all of the incubation mixture, and was carried throughout the entire procedure except for the actual incubation.

The filtered tissue was extracted in 2:1 CHCl$_3$:CH$_3$OH (10 ml) for 2 hr, and this extract, reduced almost to dryness, was recombined with the incubation supernatant. This combination in turn was extracted with ethyl acetate (2.5 ml, 3 times) at neutral pH in the presence of (NH$_4$)$_2$SO$_4$ (0.5 g/ml). The concentrated extract was applied to an alumina column in benzene. After the column was washed with benzene, the unconjugated estrogens were eluted with 100 ml ethanol and the estrogen sulfates with ethanol:water (1:1, 100 ml). The conjugated fraction was further separated from trailing free estrogens by a single development of instant thin layer chromatography (SG; chloroform:acetone:acetic acid, 110:35:6). Marker estrogen sulfates run simultaneously were identified by staining with 50% methylene blue reagent (25 mg % methylene blue in 0.05 N sulfuric acid) in acetone.

The estrogen sulfates were hydrolyzed with aryl sulfatase[3] (5 mg/10 ml) in 0.1 M sodium acetate buffer (pH 5) for two days at 37° C. (without shaking or mixing) and the estrogen moiety extracted into ether. Both the unconjugated estrogens and those hydrolyzed from sulfate esters were further purified by the procedure of Brooks et al, Biochim. Biophys. Acta, 104:250–260 (1965) and the metabolites identified and quantitated on instant thin layer chromatography (SA; chloroform:methanol, 97:3) in accordance with Pack et al (1974), supra.

Histology. Samples of tissue for histological examination were taken 3 inches from the bifurcation of each uterine horn, fixed in buffered formalin and stained by the Papanicolaou method.

B. Results

Estrogen metabolism. In earlier studies by incubation of uteri and labeled E$_2$, the only estrogen metabolites observed were estrone (E$_1$) and the 3-sulfates of both E$_2$ and E$_1$, Pack et al (1974) supra. Although the E$_2$ dehydrogenase activity was evident throughout the estrous cycle and in the immature uteri, estrogen sulfotransferase was not apparent in the immature or estrus porcine uteri. This earlier investigation had used uteri from pigs selected from a local slaughterhouse.

In the present study, wherein the reproductive history of each animal was known, the only metabolism of E$_2$ observed at metestrus in uteri from fertilized pigs was the conversion of 13.6% of the added labeled E$_2$ to E$_1$ (Table 3 below). The extent of the oxidation of E$_2$ to unconjugated E$_1$ remained fairly constant throughout these experiments (16.6±5.7% for the 25 days following fertilization). In this respect the uteri from fertilized pigs (sows or gilts) were not significantly different from uteri undergoing the normal estrous cycle, where an average 18.7±7.2% of the added E$_2$ was found as free E$_1$ regardless of the phase of the cycle.

On the other hand, sulfurylation of the 3-hydroxyl group during the 2-hour incubation, as in the non-pregnant gilt, was very low (3%) on the day of insemination. Sulfurylation then reached a maximal level by day 5 of pregnancy, and this activity was maintained for the remainder of the 25 days studied as shown in FIG. 1. The plot for sows is indicated by □—□ and that for gilts by *—*. The dotted line represents the level of estrogen sulfurylation during a normal porcine estrus cycle. After a 2-hour incubation, sulfurylation in gilt uterus reached a higher level (57.2±8.9%, 5 to 23 days following fertilization) than that in sow uterus [41.2±6.0%, 8 to 25 days following fertilization ($P < 0.05$)].

Unlike the pattern in non-pregnant gilts, estrogen sulfurylation in uteri from fertilized pigs did not cease after the time required for an estrous cycle but persisted at a maximal rate for at least 10 days more, that is, during the implantation process.

TABLE III

Metabolism of 17β-Estradiol Added to Incubates of Uteri Obtained from Fertilized Pigs

| Days Following Fertilization | Percent of Added E$_2$ Found in Various Fractions | | | | |
| --- | --- | --- | --- | --- | --- |
| | E$_1$S/E$_2$3S | Free E$_1$ | E$_2$3S | E$_1$S | Total E$_1$*** |
| 0 (S)* | — | 13.6 | — | — | 13.6 |
| 2 (G) | .46 | 15.3 | 19.4 | 8.9 | 24.2 |
| 5 (G) | 2.13 | 16.4 | 15.4 | 31.9 | 48.3 |
| 8 (S) | 4.88 | 16.4 | 5.9 | 29.9 | 46.3 |
| 10 (G) | 2.57 | 24.5 | 14.7 | 37.0 | 61.5 |
| 13 (S) | 1.70 | 12.0 | 18.6 | 31.6 | 43.6 |
| 17 (G) | .69 | 6.4 | 37.6 | 25.9 | 32.3 |
| 19 (S) | 3.17 | 25.7 | 10.0 | 31.2 | 56.9 |
| 23 (G) | 2.45 | 15.9 | 19.1 | 46.3 | 62.2 |
| 25 (S) | 2.33 | 19.9 | 11.8 | 27.3 | 47.2 |
| | 2.50 | 16.6 | 16.6 | 32.6 | 49.8 |
| | ± 1.21** | ± 5.7 | ± 9.5+ | ± 6.4+ | ± 10.1+ |
| 25 (A) | — | 12.9 | — | — | 12.9 |

*Uteri from sows (S), gilts (G) or anovulatory gilt (A).
**Mean ± Standard deviation
***Free estrone (E$_1$) plus estrone sulfate (E$_1$S).
+Mean calculated from values obtained when sulfurylation was maximal (i.e., days 5–25 following fertilization).

The continued sulfurylation of estrogen in the uterus of the pregnant pig cannot be attributed to the presence of fetal membranes because none were detected by histological examination of the tissue used for incubation. Therefore, these data from investigations with fertilized and anovulatory porcine uteri support the premise that uterine estrogen sulfurylation requires the presence of systemic progesterone. These data also show that little or no estrogen receptor complex enters the endometrial nuclei in the presence of estrogen sulfotransferase activity. See also Pack et al, "Nuclear and Cytoplasmic Estrogen Receptor in Gilt Endometrium Throughout the Estrous Cycle," Endocrinology, in press (1978) and the references cited therein. Therefore, the absence of this complex may permit progesterone in association with its receptor during nuclear interaction to convert proliferative tissue into secretory tissue. Sulfurylation, in conjunction with increased E$_2$-dehydrogenase activity, may be the mechanism by which the estrogen is metabolized and removed from the cell so as to prevent the E$_2$ receptor complex from forming and continuing the proliferative process. The resulting secretory endometrium, as corroborated in the histological study, is a condition related to implantation.

EXAMPLE 3

Cyclic Relationship of Estrogen Sulfurylation in Human Endometrial Curettings

A. Materials and Methods

Radioisotopes. [6,7-$^3$H]E$_2$ and [2,4,6,7-$^3$H]E$_2$ were obtained from New England Nuclear Corp., Boston, Mass., and purified on ITLC-SA (Gelman Instrument Co.) with CHCl$_3$:CH$_3$OH (97:3) as the developing solvent. Na$_2$$^{35}$SO$_4$ was obtained from New England Nuclear Corp. and used directly from the bottle.

Human endometria. Endometrial specimens (60–1500 mg) were gathered from the operating room at the time of surgery and placed in 0.9% saline solution on ice. Most patients (22) were young women undergoing tubal ligations for the purpose of sterilization, two patients were having IUD's removed and eight patients (hysterectomies and laparoscopies) had normal endometria upon histological examination. All had had at least one pregnancy, had no endocrine problems, were cycling normally and were not taking any drugs, except for two patients on Librium ® and two on Aldoril ®. Ages ranged from 23 to 48 years, the average being 31±5 years.

Metabolism. Amounts varying from 55 to 400 mg of endometrium were incubated in 2.5 ml of modified bicarbonate buffer with 10 µl of [6,7-$^3$H]$E_2$ ($3 \times 10^{-9}$M) and 100 µl of $Na_2{}^{35}SO_4$ ($1 \times 10^{-4}$M). The remainder of the procedure was the same as described for gilt uterus in Example 2

B. Results

Determination of the estrogen sulfotransferase and $E_2$ dehydrogenase activities and the nuclear migration of estrogens in human endometrium (endometrial curettings) during the different phases of the menstrual cycle. Experiments with human endometrium indicated that the extent of oxidation or sulfurylation of the [$^3$H]$E_2$ was independent of the amount of tissue between 55 and 329 mg per incubation (Table IV). Apparently, in the incubations described herein, the tissue enzymes were not limiting during the 2-hour experiments.

These experiments demonstrated the formation of $E_2$ 3-sulfate and $E_1$ sulfate by secretory human endometrium. The presence of estrogen sulfotransferase only in the secretory endometrium agrees with data obtained with porcine uteri [Pack et al (1974) supra.] The stimulated synthesis of estrogen sulfates in the secretory endometrium (days 16–24) was accompanied by a decreased level of nuclear estrogen receptor (0.41±0.20 fmoles/µg DNA) relative to that in nuclei from the proliferative endometrium (1.30±0.17 fmoles/µg DNA). As observed in the porcine studies, the highest nuclear receptor levels in human endometria were found when estrogen sulfotransferase activity was very low (proliferative phase, days 8–13).

The limitations of histologically dating the curettings made it impossible to segregate specimens from women within 48 hours post-ovulation. However, three endometrial curettings obtained at days 14 and 15 displayed 2.3, 4.3 and 15% sulfurylation of the [$^3$H]$E_2$. These same specimens showed 70, 75 and 93% oxidation, respectively, of the labeled $E_2$ to $E_1$ plus $E_1$ sulfate.

TABLE IV

Oxidation and Sulfurylation of Tritiated $E_2$ During Incubations[1] with Varying Amounts of Human Indometrium

| Stage of Menstrual Cycle | Milligrams of Tissue | Percent of Tritiated $E_2$ | |
|---|---|---|---|
| | | Oxidized to Estrone | Sulfurylated |
| Proliferative days 4–7 | 55 | 29 | 0 |
| | 118 | 47 | 0 |
| | 329 | 45 | 0 |
| Secretory day 24 | 60 | 78[2] | 36 |
| | 120 | 82[2] | — |
| | 300 | 82[2] | 21 |

[1]Incubations were carried out for 2 hours as described in Materials and Methods with $3 \times 10^{-9}$M tritiated $E_2$.
[2]These values represent $E_1$ + $E_1$ sulfate, which only occurs in the secretory phase.

It appears that endometrial estrogen sulfotransferase was not activated immediately after ovulation. The results of these experiments are shown in FIG. 2, wherein $O_2$ represents oxidation of 17β-estradiol to estrone plus estrone sulfate (secretory phase only) and $SO_4$ the total sulfurylation of estrogens. Brackets indicate standard deviation from the mean.

These experiments with human endometrial curettings demonstrate that estrogen sulfotransferase activity is greatly stimulated during the secretory phase and that this increased metabolism of $E_2$ is accompanied by a decreased uptake of the nuclear receptor complex.

EXAMPLE 4

Effect of 4-Nitroestrogens on the Binding of 17β-estradiol ($E_2$) by Rabbit Uterine Tissue Competitive binding experiments were carried out utilizing the 100,000×g supernatant from rabbit uterus maintained at 4° C. Unlabeled competitive estrogens were added to the incubation 10 min. before tritiated 17β-estradiol. Incubations were carried out in quadruplicate for 2 h on ice. [2,4,6,7-$^3$H]-17-Estradiol was added to 0.5 ml of supernatant (0.69 mg protein) at a concentration of 0.7 nM. Radioactivity in the bound 17β-estradiol was assayed by the dextran-coated charcoal (1:10) procedure. The control incubations bound 2.8 fmol of 17β-estradiol per milligram of protein. At a molar ratio of 10:1, 3-methoxy-4-nitroestrone (3-methoxy-4-$NO_2$-1,3,5(10)-estratriene-17-one) blocked >90% of the activity of estrogen sulfotransferase. Moreover, even when a 2000-fold excess of 3-methoxy-4-nitroestrone is employed, binding of 17β-estradiol to its receptor is not blocked.

EXAMPLE 5

Preparation of a Longlasting Troche

Troches (1500), each weighing 750 mg, were formulated as follows:

| | Ingredient | Gms. |
|---|---|---|
| (a) | 3-Methoxy-4-nitroestrone | 15.0 |
| (b) | Pectin | 370.0 |
| (c) | Gelatin | 370.0 |
| (d) | Sodium carboxymethylcellulose | 370.0 |

The diol was mixed with approximately 10 gm. of pectin. The remainder of the pectin and other ingredients were added and mixed thoroughly. The resulting mixture was compressed into capsule-shaped troches, each of which contained 10 mg of 3-methoxy-4-nitroestrone.

EXAMPLE 6

Preparation of a Hard Candy Lozenge

The following formulation can be used to prepare approximately 9,000 lozenges weighing 5.0 grm. each.

| | Ingredient | Weight |
|---|---|---|
| (a) | 2,4-Dibromo-1,3,5(10)-estratriene-3,17β-diol | 90 gms. |
| (b) | Sodium cyclamate | 450 gms. |
| (c) | Saccharin sodium | 45 gms. |
| (d) | Cetyl diethyl benzyl-ammonium chloride | 27 gms. |
| (e) | Benzocaine | 45 gms. |
| (f) | Granular sugar | 28 kgs. |
| (g) | Liquid glucose (43°) | 16.7 kgs. |
| (h) | Sour orange flavor q.s. Wild cherry flavor q.s. | |

The granular sugar is placed into a pre-cook kettle with 14 liters of water. The mixture is brought to a boil and the sodium cyclamate is added and dissolved with stirring. Glucose is added and the mixture brought to a predetermined temperature of 135° C.

The composition is transferred to a continuous vacuum cooker and reduced to a proper consistency for a candy base, to which the remaining ingredients are added with stirring. The mixture is thoroughly kneaded and a continuous rope formed. Lozenges weighing about 5.0 gm. each and containing about 10.0 mg. of 2,4-dibromo-1,3,5(10)-estratriene-3,17β-diol are cut from the rope, packaged and distributed in any convenient manner.

EXAMPLE 7

Preparation of an Ointment Formulation

One thousand grams of an ointment for topical application containing 1.0% of 2,4-dinitro-1,3,5(10)-estratriene-3,17β-diol are prepared as follows:

|     | Ingredient | Gms. |
| --- | --- | --- |
| (a) | 2,4-Dinitro-1,3,5(10)-estratriene-3,17β-diol | 10 |
| (b) | Light liquid petrolatum | 250 |
| (c) | Wool fat | 200 |
| (d) | White petrolatum q.s. ad | 1000 |

The wool fat, white petrolatum and 200 gms. of the light liquid petrolatum are liquefied and held at 43° C. The active ingredient is mixed with the remaining liquid petrolatum and passed through a colloid mill. After passing through the mill, the mixture is stirred into the melt. The melt resulting is permitted to cool with continued stirring until congealed.

EXAMPLE 8

Preparation of a Vaginal Foam

One hundred containers of an aerosol foam for vaginal use each containing 1.0% of 2-nitro-1,3,5(10)-estratriene-3,17β-diol are prepared as follows:

|     | Ingredient | Gms. |
| --- | --- | --- |
| (a) | 2-Nitro-1,3,5(10)-estratriene-3,17β-diol | 30 |
| (b) | Polyoxyethylated high molecular weight fatty alcohol | 10 |
| (c) | Oleate ester of sorbitol | 30 |
| (d) | Propellant | 300 |
| (e) | Propylene glycol q.s. ad | 3000 |

Polyoxyethylated high molecular weight fatty alcohol foaming agent is dissolved in the propylene glycol vehicle. The 2-nitro-1,3,5(10)-estratriene-3,17β-diol is dispersed with sorbitol oleate surfactant with gentle heating, if necessary, and added to the propylene glycol solution. One hundred aerosol containers of appropriate volume are filled with equal aliquots, capped with an aerosol valve and gassed with a propellant mixture of 4 parts of dichlorotetrafluoroethane to 1 part of dichlorodifluoromethane.

From the foregoing description, one skilled in the art can easily ascertain the essential characteristics of this invention, and without departing from the spirit and scope thereof, can make various changes and modifications of the invention to adapt it to various usages and conditions. Consequently, such changes and modifications are properly, equitably, and intended to be, within the full range of equivalence of the following claims.

What is claimed is:

1. A unit dosage pharmaceutical composition for the prevention of implantation of a blastocyst in the epithelial uterine lining of a mammal female and possessing a total per unit dosage of an accurate predetermined amount of an estrogen sulfotransferase inhibiting compound such that said dosage is administered daily for from 3 to 9 days in quantities each day of from 0.1 to 500 mg of the compound.

2. A composition according to claim 1, wherein the estrogen sulfotransferase inhibiting compound is a compound selected from the group consisting of the formula wherein $R_1$ is Br, $NO_2$ or H; $R_2$ is Br, $NO_2$, $NH_2$, or H; R is H or alkyl of 1-4 carbon atoms, inclusive; $R_3$ is O or $H_2$; $R_4$ is $H_2$, O or α-H, β-OH, and $R_5$ is $H_2$; αH, β-OH or βH, α-OH with the proviso that $R_1$, $R_2$, and $R_3$ cannot all be hydrogen.

3. The composition of claim 2, wherein R is $CH_3$ and $R_4$ is α-H; β-OH.

4. The composition of claim 2, wherein $R_1$ and $R_2$ are $NO_2$.

5. The composition of claim 2, wherein $R_1$ and $R_2$ are Br.

6. The composition of claim 2, wherein R is $CH_3$, $R_1$ is H and $R_4$ is α-H, β-OH.

7. The composition of claim 2, wherein R is $CH_3$ and $R_4$ is O.

8. The composition of claim 2, wherein the compound is 2,4-dibromo-1,3,5(10)-estratriene-3,17β-diol.

9. The composition of claim 2, wherein the compound is 4-nitro-1,3,5(10)-estratriene-3,17β-diol.

10. The composition of claim 2, wherein the compound is 3-methoxy-4-nitroestrone.

11. The composition of claim 1, wherein the amount of the compound is such that said dosage is administered daily for from 6 to 8 days in quantities each day of from 0.1 to 500 mg of the compound.

12. A method of treating a female mammal to prevent implantation of a blastocyst, which method comprises administering an effective dosage of an estrogen sulfotransferase inhibiting compound.

13. A method according to claim 12 wherein the estrogen sulfotransferase inhibiting compound is a compound selected from the group consisting of the formula wherein $R_1$ is Br, $NO_2$, or H; $R_2$ is Br, $NO_2$, $NH_2$ or H; R is H or alkyl of 1–4 carbon atoms, $R_3$ is O or $H_2$; $R_4$ is $H_2$, O or α-H, β-OH and $R_5$ is $H_2$; α-H, β-OH or β-H, α-OH with the proviso that $R_1$, $R_2$, and $R_3$ cannot all be hydrogen.

14. The method of claim 13 wherein R is $CH_3$ and $R_4$ is α-H, β-OH.

15. The method of claim 13 wherein $R_1$ and $R_2$ are $NO_2$.

16. The method of claim 13 wherein $R_1$ and $R_2$ are Br.

17. The method of claim 13 wherein R is $CH_3$, $R_1$ is H and $R_4$ is α-H, β-OH.

18. The method of claim 13 wherein R is $CH_3$ and $R_4$ is O.

19. The method of claim 13 wherein the compound is 2,4-dibromo-1,3,5(10)-estratriene-3,17β-diol.

20. The method of claim 13 wherein the compound is 4-nitro-1,3,5(10)-estratriene-3,17β-diol.

21. The method of claim 13 wherein the compound is 3-methoxy-4-nitroestrone.

22. The method of claim 12 wherein administration of an effective dosage is one in which from 0.1 to 500 mg is administered daily for 3 to 9 days immediately prior to the nidation (period of implantation of a blastocyst) period of the mammals menstrual cycle.

23. The method of claim 22 wherein the said dosage is administered daily for 6 to 8 days.

24. The method of claim 12 wherein the female mammal is a higher primate and the estrogen sulfotransferase inhibiting compound is administered on days 18 through 23 of the menstrual cycle, counting the onset of the previous menstruation as the first day of the menstrual cycle.

* * * * *